(12) United States Patent
Kauffman et al.

(10) Patent No.: US 6,339,112 B1
(45) Date of Patent: Jan. 15, 2002

(54) RADIATION CURABLE COMPOSITIONS COMPRISING METALLOCENE POLYOLEFINS

(75) Inventors: Thomas F. Kauffman, Woodbury; John P. Baetzold, North St. Paul; Margarita Acevedo, Minneapolis, all of MN (US)

(73) Assignee: H.B. Fuller Licensing & Financing Inc., St. Paul, MN (US)

( * ) Notice: Subject to any disclaimer, the term of this patent is extended or adjusted under 35 U.S.C. 154(b) by 0 days.

(21) Appl. No.: 09/191,612

(22) Filed: Nov. 13, 1998

Related U.S. Application Data (60) Provisional application No. 60/065,310, filed on Nov. 13, 1997.

(51) Int. Cl.$^7$ .......................... C08F 2/50; C09D 123/08; C08L 23/08; C08J 3/28
(52) U.S. Cl. .......................... 522/95; 522/110; 522/111; 522/112; 522/113; 522/148; 522/158; 522/159; 522/161; 522/120; 522/121; 522/46; 522/36; 522/39; 522/149; 526/348; 526/348.2; 526/348.3; 526/348.4; 526/348.5; 526/348.6; 526/348.7
(58) Field of Search .............................. 522/110, 111, 522/112, 148, 149, 158, 161, 113, 120, 121, 95, 159, 36, 39, 46; 526/126, 170, 171, 348, 348.2, 348.3, 348.4, 348.5, 348.6, 348.7

(56) References Cited

U.S. PATENT DOCUMENTS

| | | |
|---|---|---|
| 4,485,226 A | 11/1984 | Noll et al. |
| 5,112,882 A | 5/1992 | Babu et al. |
| 5,202,361 A | 4/1993 | Zimmerman et al. |
| 5,209,971 A | 5/1993 | Babu et al. |
| 5,298,708 A | 3/1994 | Babu et al. |
| 5,397,843 A | 3/1995 | Lakshmanan et al. |
| 5,407,970 A | 4/1995 | Peterson et al. |
| 5,530,054 A | 6/1996 | Tse et al. |
| 5,548,014 A | 8/1996 | Tse et al. |
| 5,559,164 A | 9/1996 | Babu et al. |

FOREIGN PATENT DOCUMENTS

| | | | |
|---|---|---|---|
| EP | 0301516 | 2/1989 | |
| EP | 0 620 247 A1 | 4/1994 | |
| EP | 0707954 | 4/1996 | |
| EP | 0 707 954 A3 * | 4/1996 | ........... B32B/27/08 |
| EP | 0738927 | 10/1996 | |
| EP | 0891991 | 1/1999 | |
| EP | 0891993 | 1/1999 | |
| WO | WO 93/11184 | 6/1993 | |
| WO | WO 96/20919 | 7/1996 | |
| WO | WO 98/45344 | 10/1998 | |

\* cited by examiner

Primary Examiner—Susan W. Berman (57) ABSTRACT

The present invention relates to radiation curable compositions comprising at least one metallocene polyolefin. The radiation curable compositions are useful for a variety of applications, particularly as coatings and adhesives. The radiation curable composition may comprise a single metallocene polyolefin, or blend thereof. The ultraviolet curable compositions further comprise at least one photoinitiator and/or at least one photoinduced coupling agent. For pressure sensitive adhesive applications, the radiation curable composition also preferably comprises other ingredients such as a tackifying resins and plasticizers.

26 Claims, 3 Drawing Sheets

RADIATION CURABLE COMPOSITIONS COMPRISING METALLOCENE POLYOLEFINS

REFERENCES TO RELATED APPLICATIONS

Figure 1:
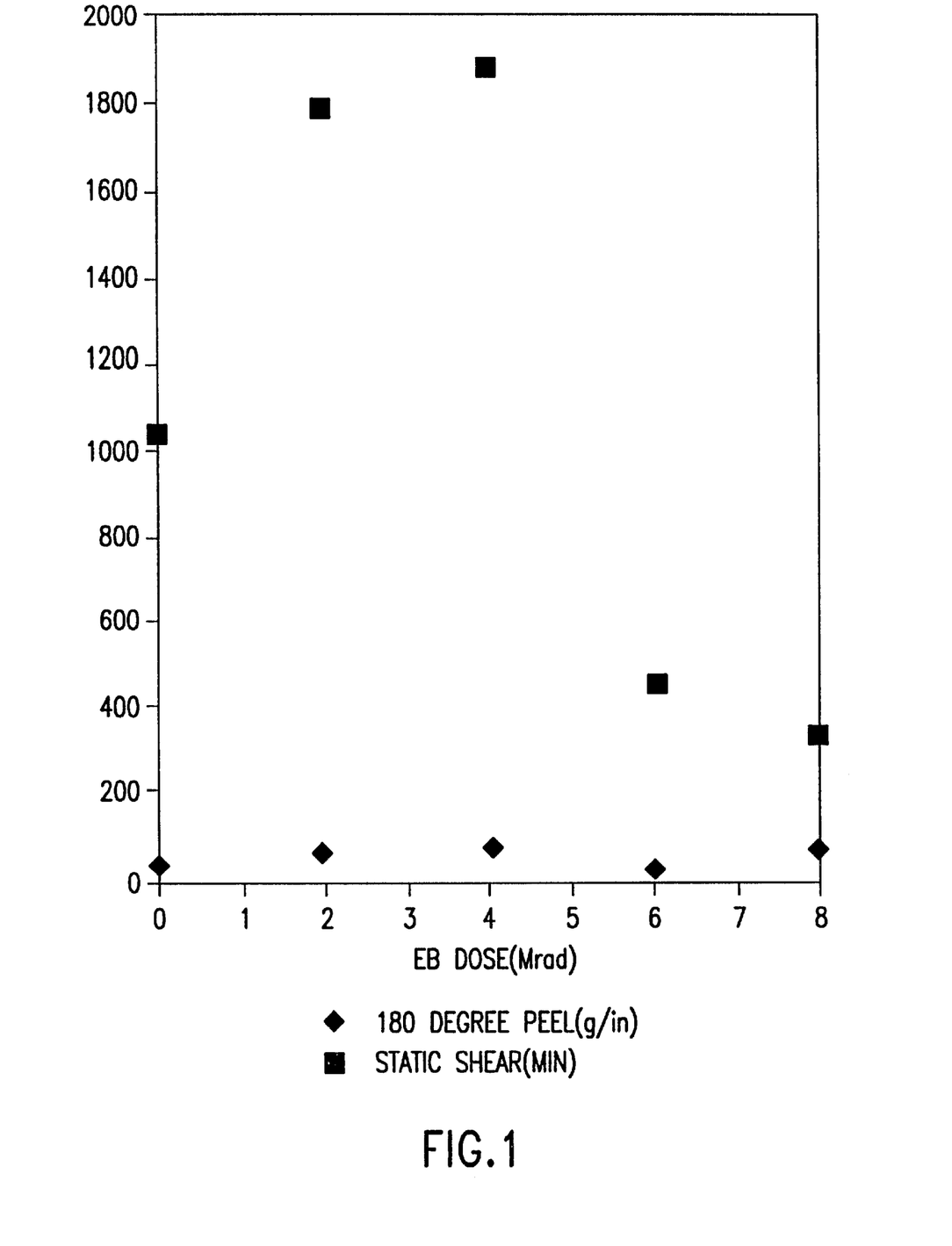
Figure 2:
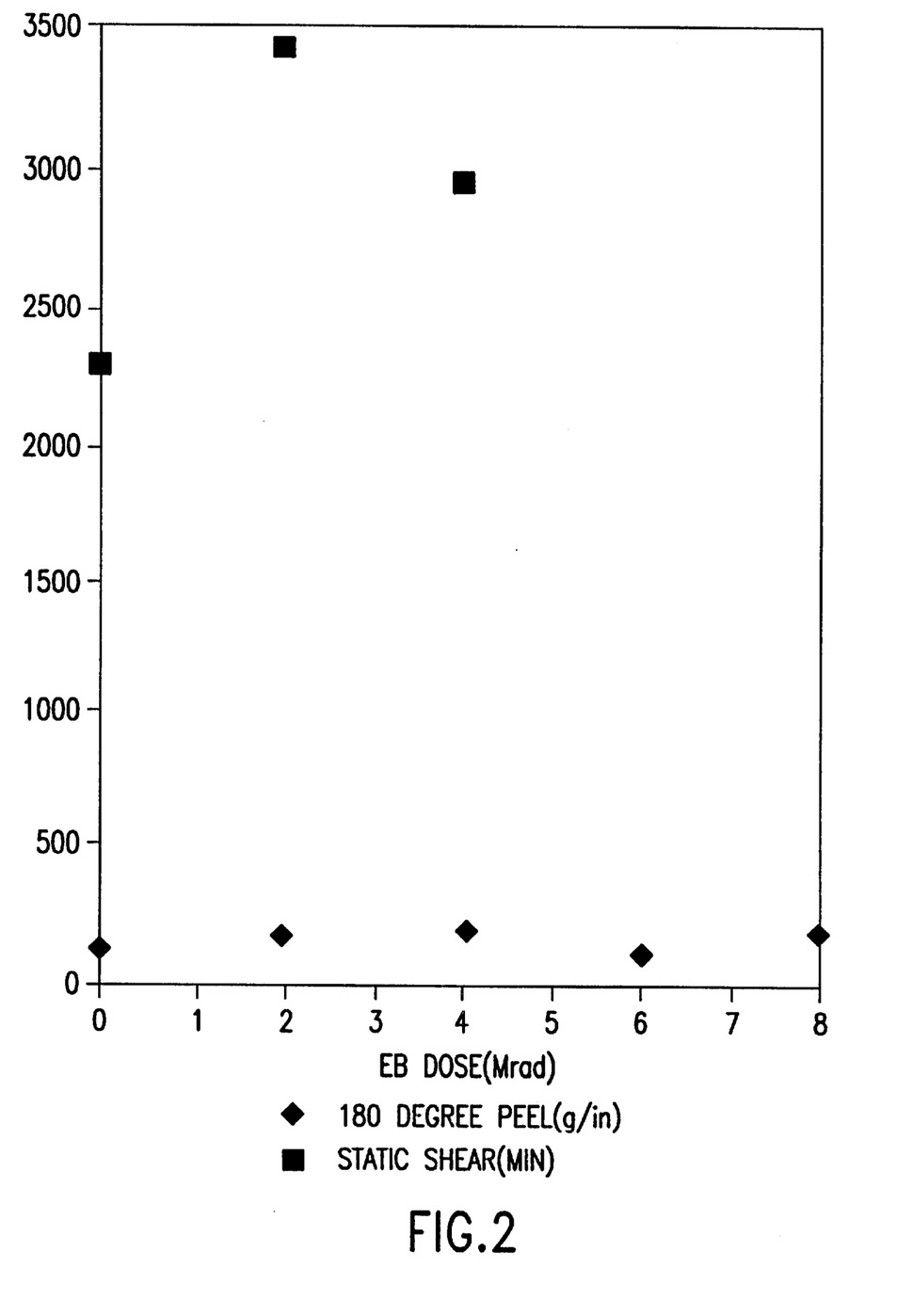
Figure 3:
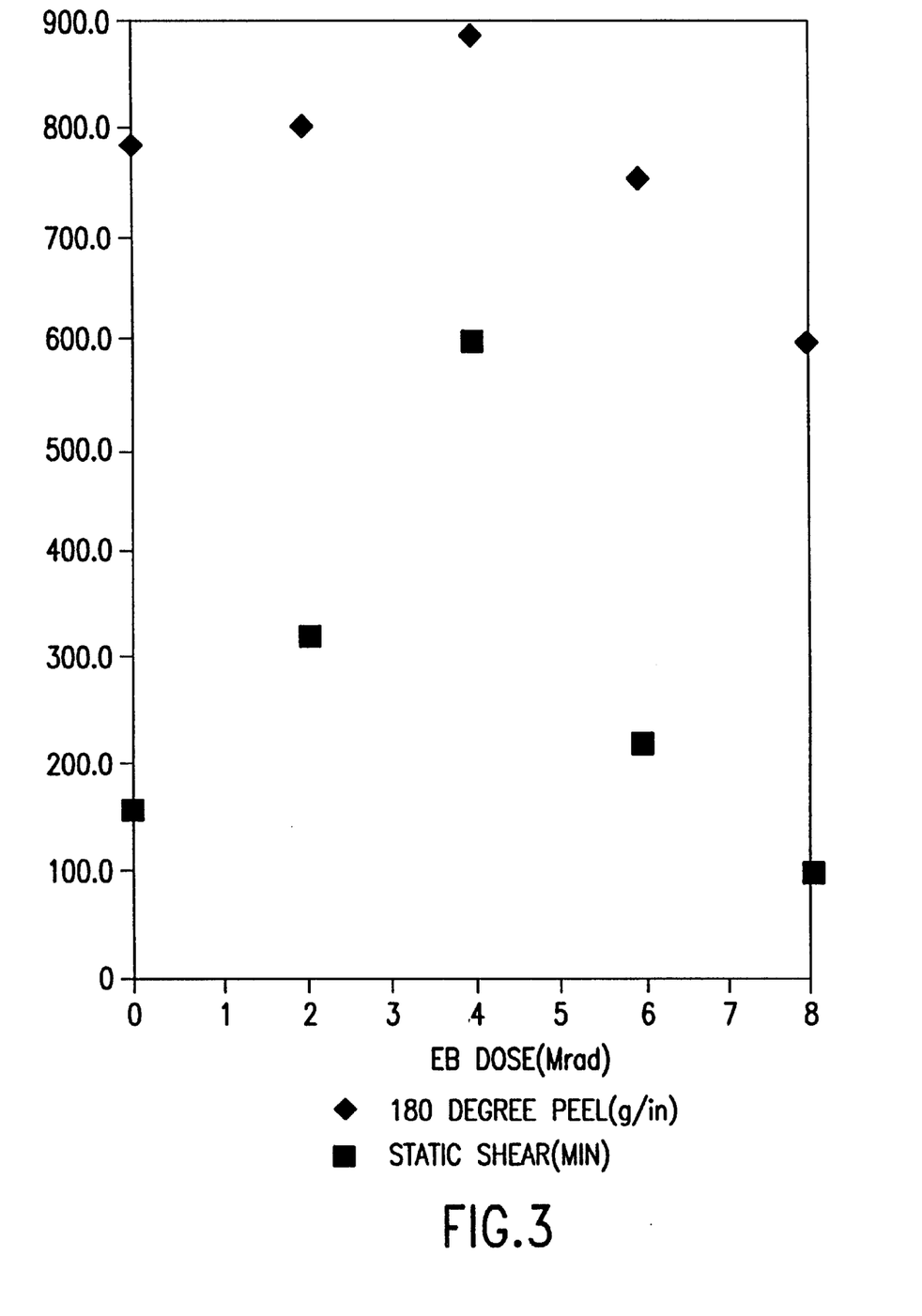

This is a Continuation-In-Part of U.S. Provisional Patent Application No. 60/065,310 filed Nov. 13, 1997.

FIELD OF THE INVENTION

The present invention relates to radiation curable compositions comprising at least one metallocene polyolefin. The radiation curable compositions are useful for a variety of applications, particularly as coatings and adhesives. The radiation curable composition may comprise a single metallocene polyolefin, or blend thereof. The ultraviolet curable compositions further comprise at least one photoinitiator and/or at least one photoinduced coupling agent. For pressure sensitive adhesive applications, the radiation curable composition also preferably comprises other ingredients such as a tackifying resins and plasticizers.

BACKGROUND OF THE INVENTION

A continuing need in the coatings and adhesive art, particularly for pressure-sensitive adhesives (PSA's), is the achievement of better control over various mechanical and process properties so that adhesives can be "tailor-made" for specific, highly demanding end-use applications such as packaging, medical, and masking tapes. These applications require a proper balance of properties, and this balance changes with the particular end-use. Similarly, laminating adhesives and coatings are needed which have low volatile content, immediate cure, and excellent adhesion to a variety of substrates, particularly film.

With the discovery of Ziegler-Natta catalysts, it became possible to polymerize α-olefin monomers to high molecular weight. The homopolymers of the $C_6$–$C_{10}$ α-olefins were naturally tacky and therefore good candidates for PSA's since they had low toxicity, good aging, and favorable oxidative stability. These homopolymers are chemically inert, resistant to plasticizer migration, and relatively inexpensive. Such homopolymers, however, exhibit poor cohesive strength, lacking the shear adhesion necessary for high performance PSA's.

There are several patents directed toward adhesive compositions comprising Ziegler-Natta catalyst derived polymerized α-olefin monomers. Initially, such amorphous polyolefins were used alone or combined with other ingredients to produce hot melt adhesives. Since the amorphous polyolefins used for hot melt adhesives tended to exhibit diminished rather than enhanced shear strength upon exposure to radiation, new combinations of α-olefin monomers that cross-link upon being exposed to radiation were developed.

For example, U.S. Pat. No. 5,112,882, issued to Babu, May 12, 1992; U.S. Pat. No. 5,209,971 issued to Babu, May 11, 1993, as well as WO 93/11184, published Jun. 10, 1993 and EP 0 620 247 A2 published Oct. 19, 1994, teach pressure sensitive adhesive compositions comprising one or more poly(α-olefin) homopolymers, copolymers, terpolymers and tetrapolymers derived from monomers containing 6 to 10 carbon atoms and photoactive crosslinking agents; whereas U.S. Pat. No. 5,298,708, issued to Babu, Mar. 29, 1994, is directed toward a microwave-active tape employing the adhesive composition of the '882 patent.

U.S. Pat. No. , 5,202,361, issued to Zimmerman et al., Apr. 13, 1993, teaches radiation-curable, tackifier free compositions containing a blend of certain acrylate esters and monoethylenically-unsaturated copolymerizable monomers, certain α-olefin polymers, and a photoinitiator.

U.S. Pat. No. 5,407,970, issued to Peterson et al., Apr. 18, 1995, teaches adhesive compositions comprising terpolymers $C_6$ to $C_{10}$ unsaturated α-olefin monomers, $C_2$ to $C_5$ α-olefin monomers, polyene monomers and an effective amount of photoactive cross-linking agent.

U.S. Pat. No. 5,559,164, issued to Babu, Sep. 24, 1996, teaches compositions radiation curable to pressure sensitive adhesives comprising one or more copolymers of α-olefin of which 90.1 to 99 mole percent are one or more straight chain α-olefins, having 2 to 10 carbon atoms of which at least 55% have 6 to 10 carbon atoms, and 9.9 to 0.1 mole percent are one or more α-olefins having 6 to 20 carbon atoms and at least one methylidyne; an effective amount of a photoactive hydrogen abstracting agent; and optionally a tackifying resin.

"Metallocene polyolefins" have recently been introduced. Metallocene polyolefins are homogeneous linear and substantially linear ethylene polymers prepared using single-site or metallocene catalysts.

Tse et al., U.S. Pat. No. 5,530,054, claims a hot melt adhesive composition consisting essentially of: (a) 30–70 wt-% of a copolymer of ethylene and about 6 to about 30 wt-% of a $C_4$ to $C_{20}$ α-olefin produced in the presence of a catalyst composition comprising a metallocene and an alumoxane and having an $M_w$ of from about 20,000 to about 100,000; and (b) a hydrocarbon tackifier which is selected from a recited list. Exemplified are compositions consisting of 45 wt-% of ethylene/butene-1 copolymer having a specific gravity of either 0.898 g/cm$^3$ or 0.901 g/cm$^3$.

Tse et al, U.S. Pat. No. 5,548,014, claims a hot melt adhesive composition comprising a blend of ethylene/α-olefin copolymers wherein the first copolymer has a $M_w$ from about 20,000 to about 39,000 and the second copolymer has a $M_w$ from about 40,000 to about 100,000. Each of the hot melt adhesives exemplified comprises a blend of copolymers, contains 45 wt-% copolymer, with at least one of the copolymers having a polydispersity greater than 2.5. Furthermore, the lowest density copolymer exemplified has a specific gravity of 0.894 g/cm$^3$.

Lakshmanan et al., U.S. Pat. No. 5,397,843, teaches blended polymer compositions comprising an admixture of a copolymer of ethylene and an α-olefin and an amorphous polypropylene and/or amorphous polyolefin, or mixtures thereof. The single α-olefin exemplified is "Flexomer 9042" from Union Carbide, having a 1-butene content of 15 wt-%, a melt index of 5.0 g/10 min., a crystallinity level of 26% and a density of 0.900 g/cm$^3$. The "Flexomer" polyolefin depicted in the examples is believed to a have a polydispersity greater than 2.5.

Hence, metallocene polyolefins also found utility for use in finished hot melt adhesive compositions. Although such compositions are believed to be a substantial improvement over the amorphous polyolefins prepared using Ziegler-Natta catalysts, such compositions continue to suffer from poor shear adhesion strength.

There exists a need for adhesive compositions having improved shear strength that can be produced from commercially available materials. The present inventors have now discovered that adhesive compositions based on metallocene polyolefins may be radiation cured to enhance their adhesive properties, particularly shear strength. The resulting adhesive compositions are relatively inexpensive in comparison to the radiation curable compositions of the prior art, since it is not necessary for the adhesive manufacturer to first polymerize the α-olefins. Further, the novel adhesive compositions are surmised to exhibit a balance of properties which is superior to those which have been previously attained.

SUMMARY OF THE INVENTION

The present invention describes metallocene polyolefin-based compositions that consistently crosslink to a reproducible extent upon exposure to a radiation source, thus substantially improving the properties of such compositions, such as the cohesive strength. Surprisingly, the metallocene polyolefin employed may have a significantly lower comonomer content relative to the α-olefin based radiation curable compositions of the prior art. Further, the applicants have found that certain commercially available grades of metallocene polyolefins exhibit a significant increase in static shear upon exposure to radiation while concurrently retaining or improving the peel values.

Accordingly, the present invention is a radiation curable composition comprising at least one metallocene polyolefin. The radiation curable composition may comprise a single metallocene polyolefin or blends thereof. Preferably, the radiation curable composition comprises from about 15 wt-% to 100 wt-% of a metallocene polyolefin having a comonomer content ranging from about 10 mole-% to about 20 mole-%. The comonomer content of the metallocene polyolefin may also be expressed in terms of weight percent. Accordingly, the radiation curable composition of the present invention comprises at least one metallocene polyolefin having a comonomer content ranging from about 30 wt-% to about 50 wt-%.

Metallocene polyolefins having comonomer contents outside the range specified above may also be employed provided the comonomer content of the metallocene polyolefin blend meets the specified range.

In the case of ultraviolet (UV) curing, the radiation curable composition further comprises at least one photoinitiator and/or photoactive coupling agent.

The composition may have some degree of adhesive properties prior to curing which are enhanced upon exposure to a radiation source. However, in most instances the composition has poor adhesive and/or coating properties until after curing. In this instance, the composition is best described as an "adhesive precursor" or "coating precursor".

In one aspect, the present invention is a composition radiation-curable to a coating wherein the coating composition comprises at least one metallocene polyolefin. The radiation curable composition may be applied to various materials and substrates such as films and metals and cured to provide a coating with desired properties such as high cohesive strength, resistance to chemicals such as solvent, resistance to oxidative degradation, abrasion resistance, improved barrier properties, as well as combinations of such properties.

In another aspect, the present invention is a composition radiation curable to an adhesive. After curing the adhesive composition may be pressure-sensitive or alternatively relatively tack-free. The adhesive may further comprises additional ingredients such as tackifiers, plasticizers, additional polymers, and additional radiation responsive materials such as unsaturated polymers, oligomers, and monomers.

In another aspect, the present invention is a thermoplastic composition radiation curable to a film. In this embodiment, the composition may comprise additives commonly used in films, particularly slip agents. The composition may be coated onto a release liner or release coated belt, cured and stripped from the belt forming a type of cast film.

Additionally, the present invention relates to method of using a radiation curable composition comprising the steps of:
  a) providing a composition comprising at least one metallocene polyolefin;
  b) coating said composition onto a substrate; and
  c) exposing said composition to an effective amount of radiation for curing.

Furthermore, the present invention also relates to a variety of articles such as medical tapes, masking tapes, pressure sensitive labels, laminates of polymeric film and foils, and industrial tapes comprising a substrate coated with a radiation cured composition, wherein said composition comprises at least one metallocene polyolefin.

DETAILED DESCRIPTION OF THE INVENTION

Metallocene polyolefins are homogeneous linear and substantially linear ethylene polymers prepared using single-site or metallocene catalysts. Homogeneous ethylene polymers are characterized as having a narrow molecular weight distribution and a uniform short-chain branching distribution. In the case of substantially linear ethylene polymers, such homogeneous ethylene polymers are further characterized as having long chain branching. Substantially linear ethylene polymers are commercially available from The Dow Chemical Company as Affinity™ polyolefin plastomers, which are produced using Dow's Insite™ technology. Homogeneous linear ethylene polymers are available from Exxon Chemical Company under the trade name Exact® plastomers.

The radiation curable composition of the present invention comprises at least one metallocene polyolefin such as homogeneous ethylene/α-olefin interpolymers which are interpolymers of ethylene and at least one $C_3$–$C_{20}$ α-olefins and particularly branched $C_3$–$C_{20}$ α-olefins. The term "interpolymer" is used herein to indicate a copolymer, or a terpolymer, or a higher order polymer. That is, at least one other comonomer is polymerized with ethylene to make the interpolymer.

The homogeneous ethylene/α-olefin interpolymer is a homogeneous linear or substantially linear ethylene/α-olefin interpolymer. By the term "homogenous", it is meant that any comonomer is randomly distributed within a given interpolymer molecule and substantially all of the interpolymer molecules have the same ethylene/comonomer ratio within that interpolymer. The melting peak of homogeneous linear and substantially linear ethylene polymers, as obtained using differential scanning calorimetry, will broaden as the density decreases and/or as the number average molecular weight decreases. However, unlike heterogeneous polymers, when a homogeneous polymer has a melting peak greater than 115° C. (such as is the case of polymers having a density greater than 0.940 g/cm³), it does not additionally have a distinct lower temperature melting peak.

In addition or in the alternative, the homogeneity of the polymer may be described by the SCBDI (Short Chain Branching Distribution Index) or CDBI (Composition Distribution Breadth Index), which are defined as the weight percent of the polymer molecules having a comonomer content within 50% of the median total molar comonomer content. The SCBDI of a polymer is readily calculated from data obtained from techniques known in the art, such as, for example, temperature rising elution fractionation (abbreviated herein as "TREF"), which is described, for example, in Wild et al., Journal of Polymer Science, Poly. Phys. Ed., Vol. 20, p. 441 (1982), in U.S. Pat. No. 4,798,081 (Hazlitt et al.), or in U.S. Pat. No. 5,089,321 (Chum et al.). The SCBDI or CDBI for the homogeneous ethylene/α-olefin interpolymers useful in the invention are preferably greater than 50%, more preferably greater than 70%, with SCBDI's and CDBI of greater than 90% being easily attained. It is important not to confuse the CDBI with the total weight percent of comonomer of the metallocene polyolefin. Although a certain weight percentage of molecules within a distribution have a comonomer content greater than 50% by weight, the metallocene polyolefin as a whole typically has a comonomer content of about 50 wt-% or less.

Homogeneous ethylene/α-olefin interpolymers differ from amorphous polyolefins also described as amorphous polyalphaolefins (APAO), with regard to homogeneity, molecular weight distribution ($M_w/M_n$), as well as comonomer (α-olefin) content. Amorphous polyolefins are homopolymers, copolymers, and terpolymers of $C_2$–$C_8$ α-olefins which are typically polymerized by means of processes which employ Ziegler-Natta catalysts, resulting in a relatively broad molecular weight distribution, typically greater than 4. In contrast, the homogeneous ethylene/α-olefin interpolymers useful in the inventive adhesive composition are characterized as having a narrow molecular weight distribution. The homogeneous ethylene/α-olefins have a $M_w/M_n$ of less than 4, prefeerably less than 3, more preferably from 1.5 to 2.5, even more preferably from 1.8 to 2.2, and most preferably about 2.0. Further, whereas amorphous polyolefins produced from Ziegler-Natta catalysts typically have an α-olefin concentration greater than 50 wt-%, homogeneous ethylene/α-olefin interpolymers useful in the present invention are predominantly ethylene, having a greater ethylene content than comonomer content.

Substantially linear ethylene interpolymers are homogeneous interpolymers having long chain branching. Due to the presence of such long chain branching, substantially linear ethylene interpolymers are further characterized as having a melt flow ratio ($I_{10}/I_2$) which may be varied independently of the polydispersity index, and the like, the molecular weight distribution $M_w/M_n$. This feature accords substantially linear ethylene polymers with a high degree of processability despite a narrow molecular weight distribution.

It is noted that substantially linear interpolymers useful in the invention differ from low density polyethylene prepared in a high pressure process. In one regard, whereas low density polyethylene is an ethylene homopolymer having a density of from 0.900 g/cm$^3$ to 0.935 g/cm$^3$, the homogeneous linear and substantially linear interpolymers useful in the invention require the presence of a comonomer which reduces the density to the range of from 0.855 g/cm$^3$ to 0.910 g/cm$^3$.

The metallocene polyolefins of the present invention contain pendent groups having readily reactive hydrogen atoms on tertiary carbon atoms and may contain residual unsaturation. When these polymers are exposed to radiation, such as ultraviolet (UV) in the presence of a photoinitiator and/or photoinduced coupling agent, or electron beam (EB), they crosslink leading to an improvement in the cohesive strength of the adhesive and/or coating. The metallocene polyolefin is polymerized from a comonomer having an effective amount of reactive hydrogen atoms on tertiary carbon atoms. Although, octene is the comonomer employed in the examples, better radiation responsiveness (i.e., greater increase in static shear values) is expected from metallocene polyolefins employing comonomers such as isoprene, and various branched comonomers such as 3-methyl pentene. A list of suitable comonomers that may be employed in the invention include methylidyne group-containing α-olefins having 6 to 20 or more carbon atoms. Examples include, 4-methyl-1-pentene, 5-methyl-1-hexene, 4-methyl-1-hexene, ethenylcyclopentane, 6-methyl-1-heptene, 5-methyl-1-heptene, 4-methyl-1-heptene, 4,5-dimethyl-1-hexene,4-ethyl-1-hexene, ethenylcyclohexane, 7-methyl-1-octene, 8-methyl-1-nonene, 4,6-dimethyl-1-heptene, allylcyclohexane, 2-ethenylbicyclo[2.2.1]heptane (i.e., 2-ethenylnorborane, which has three methylidyne groups), 2-ethenyl-6-methylbicyclo[2.2.1]heptane (which has four methylidyne groups), 2-ethenyl 6-methylbicyclo[2.2.1] heptane (which has four methylidyne groups), 2-(3-propenyl)bicyclo[2.2.1]heptane (i.e., propenylnorborane, which has three methylidyne groups), 3-(3-propenyl)-2,6,6-trimethylbicyclo[3.1.1]heptane (i.e., 3-propenylpinane, which has four methylidyne groups), 1-ethenylpentacyclo [4.2.0.0$^{2,5}$.0$^{3,8}$.0$^{4,7}$] octane (i.e., ethenylcubane, which has seven methylidyne groups), 1-ethenyltricyclo[3.3.1.1$^{3,7}$] decane (i.e., ethenyladamantane, which has three methylidyne groups), and 1,2-dimethyl-5-ethenyltricyclo[3.3.1.1$^{3,7}$] decane (i.e., 1,2-dimethyl-5-ethenyladamantane, which has three methylidyne groups).

Other methylidyne group-containing α-olefins that are suitable for use in the copolymers of the invention are the arylene, the catenary oxygen, and the catenary silicon group-containing α-olefins, such as, for example, 4-(1-methylethyl)-1-(3-propenyl)benzene, 4-(2-methylpropyl)-1-(3-propenyl)benzene, 2-(1-methylethyl)4-pentyl-3-propenylnaphthalene, 3-(2-methylpropoxy)-1-propene,4-(2-methylpropoxy)-1-butene, 3-cyclohexoxy-1-propene, dimethyl(1-methylethyl)-3-propenylsilane, bis(1-methylethyl)methyl-3-propenylsilane, and bis(1-methylethyl)methyl-4-butenylsilane.

A particularly preferred metallocene polyolefin contemplated for use in the invention comprises a homogeneous ethylene/α-olefin interpolymer backbone that has been grafted with high density polyethylene or a synthetic wax in an amount ranging from about 0.1–15% by weight. The incorporation of the grafted polyethylene and/or wax segment results in an immediate improvement in cohesive strength and heat resistance even prior to curing. Exposing such compositions to radiation under the appropriate conditions induces crosslinking, which in turn, further enhances such properties.

The long chain branches of substantially linear ethylene interpolymers have the same comonomer distribution as the interpolymer backbone and can be as long as about the same length as the length of the interpolymer backbone. When a substantially linear ethylene/α-olefin interpolymer is employed in the practice of the invention, such interpolymer will be characterized as having an interpolymer backbone substituted with from 0.01 to 3 long chain branches per 1000 carbons. Methods for determining the amount of long chain branching present, both qualitatively and quantitatively, are known in the art.

The molecular weight of the ethylene/α-olefin interpolymer will be selected on the basis of the desired performance attributes of the radiation curable formulation. Typically, however, the ethylene/α-olefin interpolymer will preferably have a number average molecular weight of at least 3,000, preferably at least 5,000. Typically, the ethylene/α-olefin interpolymer will preferably have a number average molecular weight of no more than 200,000, more preferably no more than 100,000, and even more preferably less than 80,000.

Ultra-low molecular weight ethylene/α-olefin interpolymers will be either ethylene homopolymers or interpolymers of ethylene and a $C_3$–$C_{20}$ α-olefin. Such interpolymers are surmised to be particularly useful for room temperature applied and low application temperature (<135° C.) applied radiation curable compositions. When the ethylene/α-olefin interpolymer has an ultra-low molecular weight, and the like, a number average molecular weight less than 11,000, the ethylene/α-olefin interpolymer leads to a low polymer viscosity but is characterized by a peak crystallization temperature which is greater than that of corresponding higher molecular weight materials of the same density. The ultra-low molecular weight ethylene/α-olefin interpolymers will have a number average molecular weight less than about 6000, preferably less than about 5000. Such homogeneous interpolymers will typically have a number average molecular weight of at least about 800, preferably at least about 1300.

The density of the metallocene polyolefin is a consequence of the type and amount of comonomer employed and will likewise be selected on the basis of the desired performance attributes of the radiation curable formulation. The metallocene polyolefin may be employed alone or compounded with additional ingredients such as waxes, plasticizers, and tackifiers. For metallocene polyolefins based on ethylene interpolymers copolymerized with comonomers such as octene, butene, and hexene, the density of the metallocene polyolefin ranges from about 0.850 $g/cm^3$ to about 0.885 $g/cm^3$. Typically, the metallocene polyolefin will have a density of no more than 0.880 $g/cm^3$, preferably no more than 0.875 $g/cm^3$, more preferably no more than 0.870 $g/cm^3$.

The MI of the metallocene polyolefin employed in the composition of the present invention is typically greater than about 0.5 g/10 min., preferably greater than about 10 g/10 min., more preferably less than about 30 g/10 min.; and most preferred, particularly for low application temperature compositions, are metallocene polyolefins having a MI ranging from about 100 to about 5000 cps at 350° F.

In the case of compounded compositions, the metallocene polyolefin will be present in the radiation curable compositions of the invention in an amount of at least 5 wt-%, preferably at least 10 wt-%, and more preferably at least about 15 wt-%. However, in other applications, such as EB curable coatings, the radiation curable composition may comprise up to 100 wt-% metallocene polyolefin.

The radiation curable composition may comprise a single homogeneous ethylene/α-olefin interpolymer. In such an embodiment, the homogeneous ethylene/α-olefin interpolymer will preferably have a density ranging from about 0.855 $g/cm^3$ to about 0.890 $g/cm^3$. When it is desired to prepare a radiation curable formulation with a minimal concentration of the homogeneous linear or substantially linear interpolymer, less than about 30 wt-%, the melt index ($I_2$ at 190° C.) of the homogeneous linear or substantially linear interpolymer will be preferably about 500 or less, more preferably about 30 or less, and most preferably less than about 10 g/10 min.

In the case of pressure sensitive adhesive radiation-curable compositions, preferred radiation curable compositions will comprise from about 10 wt-% to about 50 wt-%, preferably from about 20 wt-% to about 40 wt-% of a single homogeneous ethylene/α-olefin interpolymer.

In another embodiment, a first homogeneous ethylene/α-olefin interpolymer may be blended with a second homogeneous ethylene/α-olefin interpolymer, wherein the first and second interpolymers differ in number average molecular weight by at least about 5000, preferably at least about 10,000, and more preferably at least about 20,000. In this embodiment, the combination of the lower molecular weight and higher molecular weight components will tend to yield an intermediate storage modulus at 25° C. and an improved probe tack prior to curing.

In addition or in the alternative, a first homogeneous ethylene/α-olefin interpolymer may be blended with a second homogeneous ethylene/α-olefin interpolymer, wherein the first and second interpolymers differ in density by at least about 0.005 $g/cm^3$, preferably by at least about 0.01 $g/cm^3$. In this embodiment, particularly in the case of radiation curable pressure sensitive adhesives, as the density differential increases, the relative proportion of the higher density interpolymer will typically decrease, as the increased levels of crystallinity would otherwise tend to decrease storage modulus at 25° C. and probe tack to levels which would render them unsuitable for use as pressure sensitive adhesive applications.

In one embodiment, the radiation curable composition will comprise a blend of two homogeneous ethylene/α-olefin, the first interpolymer having a density of about 0.870 $g/cm^3$ or less and the second interpolymer having density greater than about 0.900 $g/cm^3$. In this instance, the density of the blend of metallocene polyolefins will continue to be less than about 0.885 $g/cm^3$ as described previously. For lower viscosity adhesive precursor compositions, especially those which are radiation curable at temperatures less than about 163° C. (325° F.), the second homogeneous ethylene/α-olefin interpolymer will have a greater density than the first homogeneous ethylene/α-olefin interpolymer, and will preferably have a melt index greater than about 125, more preferably greater than about 500, and most preferably greater than about 1000 g/ 10 min.

In the case of UV curing, one or more photoactive initiators and/or photoactive coupling agents are added to the composition. Hydrogen abstracting type radical initiators are preferred. Representative examples include, but are not limited to aldehydes, such as benzaldehyde, acetaldehyde, and their substituted derivatives; ketones such as acetophenone, benzophenone, and their substituted derivatives (particularly the 4-alkylbenzophenones, wherein the alkyl group has 1 to 18 carbon atoms); quinones such as benzoquinone, anthraquinone, and their substitutes derivatives, thioxanthones, such as 2-isopropylthioxanthone and 2-dodecylthioxanthone; and certain chromophore-substituted halomethyl-sym-triazines, such as 2,4-bis(trichloromethyl)-6-(3',4'-dimethoxyphenyl)-sym-triazine. Photoactive initiators that are preferred, since they are particularly effective in bringing about rapid gelation of the adhesive composition upon application of radiation, are polyfunctional benzophenones (i.e., compounds having aliphatic, aromatic, nitrogenous, silicic, or hetero atomic nuclei to which two to four benzoylphenoxy groups are attached). A particularly preferred photoactive hydrogen abstracting agent is polyfunctional derivatives of benzophenone containing at least one long chain aliphatic alcohol. A representative example is as follows:

wherein Ph is phenol and Z is selected from the group consisting of aliphatic oligomers (i.e. ethylene-butylene), methyl, ($C_{2n}H_{2n+1}$), benzophenone, and mixtures thereof. It is important to note that the above identified photoinduced couplings agents are novel in themselves and have utility in a variety of other radiation curable compositions (in the absence of metallocene polyolefins), having abstractable hydrogens such as polyester, polyacrylate, and other polyolefin based compositions.

Another suitable type of photoinitiator that may be employed in the compositions of the present invention is the "alpha cleavage type" photoinitiator. This type is particularly beneficial when other unsaturated species such as acrylated oligomers and monomers are further employed. Alpha cleavage type photoinitiators are known in the art. Commercial examples include Irgacure 184 and Darocur 1173, both available from Ciba-Giegy (Hawthorne, N.Y.).

Photoactive initiators and photoinduced coupling agents are present at a concentration of from about 0.05 wt-% to about 3 wt-%, preferably from about 0.1 wt-% to about 2.0 wt-% and more preferably from about 0.5 wt-% to about 1.5 wt-% for UV curable compositions. However, in the case of electron-beam radiation, photoactive agents are not needed to crosslink the metallocene polyolefin.

To cure the composition of the present invention, a source of actinic radiation of sufficient energy (i.e., wavelength ranges) to generate free radicals when incident upon the particular photoinitiator selected for use in composition should be chosen. The preferred wavelength ranges for photoactive hydrogen abstracting agents disclosed above is 400 to 250 nm. The amount of radiant energy required to crosslink the adhesive film or coating of the present invention is 100 to 1500 mJ/cm$^2$, more preferably 200 to 800 mJ/cm$^2$, as measured with a Power-Puck™ radiometer manufactured by EIT. Details of the photocure process are disclosed in U.S. Pat. Nos. 4,181,752 and 4,329,384.

Even in the absence of a photoactive hydrogen abstracting agent, the composition can be cured using electron-beam radiation. The dosage needed to crosslink the composition of the present invention varies depending on the particular composition but generally ranges from about 1 to 20 Mrads, preferably from about 2 to about 10 Mrads. Details of suitable processes for EB curing of adhesives-coated substrates can be found in U.S. Pat. No. 4,533,566, which is incorporated herein by reference.

In addition to or in the alternative, the radiation curable compositions of the present invention may further comprise a second solid or liquid radiation responsive material (RRM) that can polymerize or crosslink upon radiation exposure in an amount up to about 30 wt-%. Radiation responsive material contemplated for use in the invention include polyisoprene, preferably liquid; (meth) acrylated polyesters, (meth) acrylic monomers, (meth) acrylated block oligomers such as ethylenebutylene, (meth) acrylated polyolefins, (meth) acrylated urethanes, (meth) acrylated polyamides, and other oligomers and monomers. A further example of such is RRM 1, a radiation responsive material produced from reacting a hydroxy terminated ethylene-butylene liquid copolymer, such as Kraton® L-1203, available from Shell Chemical Company (Houston, Tex.), with an isocyanate terminated urethane acrylate oligomer at a 1:1.5 equivalence ratio to functionalize the OH group of the ethylenebutylene oligomer. As in the case of the above identified photoinduced coupling agent, RRM 1 is also novel in itself and has utility in a variety of other types of radiation curable compositions.

As used herein, the term "tackifier" means any of the compositions described below which are useful to impart tack to the hot melt adhesive composition. ASTM D-1878-61T defines tack as "the property of a material which enables it to form a bond of measurable strength immediately on contact with another surface".

In general terms, tackifying resins are useful in the radiation curable composition of the invention. Tackifying resins comprise resins derived from renewable resources such as rosin derivatives including wood rosin, tall oil, gum rosin; rosin esters, natural and synthetic terpenes, and derivatives of such. Aliphatic, aromatic or mixed aliphatic-aromatic petroleum based tackifiers are also useful in the foams of this invention. Representative examples of useful hydrocarbon resins includes alpha-methyl styrene resins, branched and unbranched $C_5$ resins, $C_9$ resins, $C_{10}$ resins, as well as styrenic and hydrogenated modifications of such. Tackifying resins range from being a liquid at 37° C. to having a ring and ball softening point of about 135° C. Solid tackifying resins with a softening point greater than about 100° C., more preferably with a softening point greater than about 130° C. are particularly useful to improve the cohesive strength of the adhesives of the present invention, particularly when only a single homogeneous ethylene/α-olefin interpolymer is utilized.

For the radiation curable composition of the invention, the preferred tackifying resin is predominantly aliphatic. However, tackifying resins with increasing aromatic character are also useful, particularly when a second tackifier or mutually compatible plasticizer is employed.

The radiation curable composition of the invention may comprise from about 0 wt-% to about 70 wt-% of a tackifying resin. Typically, and particularly when it is desired to employ less than about 30 wt-% of the homogeneous ethylene/α-olefin interpolymer, the radiation curable composition will comprise from about 20 wt-% to about 60 wt-%, more typically from about 30 wt-% to about 60 wt-% tackifier.

In the alternative, in cases where it is desirable to employ at least about 30 wt-% of the homogeneous ethylene/α-olefin interpolymer, the present invention advantageously provides radiation curable formulations which contain minimal tackifier, and the like, less than about 30 wt-% tackifier, preferably less than about 25 wt-% tackifier, more preferably less than about 20 wt-% tackifier, and most preferably less than about 15 wt-% tackifier. In such instances, radiation curable compositions containing less than about 10 wt-% tackifier, and even compositions having no tackifier, exhibit adequate tack for adherence to a substrate prior to curing.

A plasticizer is broadly defined as a typically organic composition that can be added to thermoplastics, rubbers and other resins to improve extrudability, flexibility, workability, or stretchability. In preferred embodiments of the invention, a plasticizer will be present in the radiation curable composition in an amount up to about 60 wt-%, particularly for compositions having relatively low peel strength. In the case of radiation curable compositions having a high degree of pressure sensitivity, the plasticizer is preferably employed in an amount ranging from about 20 wt-% to about 40 wt-%. Higher amount of plasticizer may be employed in radiation curable "oil-gels". The plasticizer may be either a liquid or a solid at ambient temperature. Exemplary liquid plasticizers include hydrocarbon oils, polybutene, liquid tackifying resins, and liquid elastomers, such as liquid polyisoprene. Plasticizer oils are primarily hydrocarbon oils which are low in aromatic content and which are paraffinic or napthenic in character. Plasticizer oils are preferably low in volatility, transparent and have as little color and odor as possible. The use of plasticizers in this invention also contemplates the use of olefin oligomers, low molecular weight polymers, vegetable oils and their derivatives and similar plasticizing liquids.

When a solid plasticizing agent is employed, it will preferably have a softening point above about 60° C. It is believed that by combining the homogeneous ethylene/α-olefin interpolymer with a suitable tackifying resin and a solid plasticizer such as a cyclohexane dimethanol dibenzoate plasticizer, the resulting radiation curable composition may be applied at temperatures below about 120° C., preferably below about 100° C. Although a 1,4-cyclohexane dimethanol dibenzoate compound commercially available from Velsicol under the trade name Benzoflex™ 352 is exemplified, any solid plasticizer that will subsequently recrystallize in the compounded thermoplastic composition is suitable. Other solid plasticizers that may be suitable for this purpose are described in EP 0422 108 B1 and EP 0 410 412 B1, both assigned to H.B. Fuller Company.

Waxes may be usefully employed in the radiation curable compositions of the present invention, particularly when the composition is intended to be relatively tack free upon cooling and solidifying, such as the protective coatings. Waxes are commonly used to modify the viscosity and reduce tack at concentrations up to about 20 wt-%, preferably less than about 10 wt-%. Waxes useful in the radiation curable compositions of the present invention include paraffin waxes, microcrystalline waxes, Fischer-Tropsch, polyethylene and by-products of polyethylene wherein $M_w$ is less than about 3000.

Also suitable are waxes prepared using a constrained geometry catalyst. Ultra-low molecular weight ethylene/α-olefin interpolymers having a relatively high density, greater than about 0.920 g/cm$^3$ may be referred to as homogeneous waxes and are set forth in the examples below. Homogeneous waxes, in contrast to paraffinic waxes and crystalline ethylene homopolymer or interpolymer waxes, will have a $M_w/M_n$ of from about 1.5 to about 2.5, preferably from about 1.8 to about 2.2.

Homogeneous waxes lead to a low polymer and formulation viscosity, but are characterized by peak crystallization temperatures which are greater than the peak crystallization temperatures of corresponding higher molecular weight materials of the same density. In adhesive applications, the increase in peak crystallization temperature translates to an increased heat resistance, and the like, improved creep resistance in pressure sensitive adhesive foam, and improved shear adhesion failure temperatures (SAFT) in the uncured adhesive composition.

As is known in the art, various other components can be added to modify the tack, color, odor, etc., of the radiation curable thermoplastic composition. Additives such as anti-block additives, pigments, and fillers, can also be included in the formulations. It is generally preferred that the additives should be relatively inert and have negligible effects upon the properties contributed by the homogeneous linear or substantially linear interpolymer, tackifying agent, and plasticizer.

The metallocene polyolefins of the present invention can be produced in accordance with any known polymerization process, including slurry, or solution phase polymerization, gas phase polymerization, and high pressure polymerization process. Solution phase polymerization is surmised to most amenable to branched comonomers and those having relatively larger molecular structure. Alternatively, branched comonomers such as 3-methyl-pentene, 4-methyl-heptene and 4,5 dimethyl 1-hexene, as well as high density polyethylene or waxes may be grafted onto an ethylene backbone. Grafting can be achieved by feeding the metallocene polyolefins and the material to be grafted (i.e. high density polyethylene) in the presence of a suitable free radical generator such as peroxide into a melt extruder. More information pertaining to the characteristics and polymerization of grafted ethylene α-olefin polymers, can be found in U.S. Pat. No. 5,126,199 and U.S. Pat. No. 5,185,199, incorporated herein by reference, both assigned to The Dow Chemical Company.

After polymerization of the metallocene polyolefins containing branched comonomers such as 3-methyl-pentene, 4-methyl-heptene and 4,5dimethyl 1-hexene, as well as high density polyethylene or wax, the polymer would then optionally be combined with tackifiers and plasticizers at the amounts previously specified. The resulting composition could then be coated onto Mylar™ at a thickness of about 1 mil and exposed to a EB radiation source. Alternatively, a photoinitiator and/or photoinduced coupling agent may be further added and the resulting composition exposed to UV.

The radiation curable compositions of the invention may be prepared by standard melt blending procedures. In particular, the first polymer(s), tackifier(s), and optional plasticizer(s) may be melt blended at an elevated temperature (from 150° C. to 200° C.) under an inert gas blanket until a homogeneous mix is obtained. Any mixing method producing a homogeneous blend without degrading the hot melt components is satisfactory, such as through the use of a heated vessel equipped with a stirrer.

Further, the homogeneous ethylene/α-olefin interpolymer (s), optional tackifier(s) and optional plasticizer(s) may be provided to an extrusion coater for application to the substrate.

When the ethylene/α-olefin interpolymer is a blend of two or more ethylene/α-olefin interpolymers, it will be preferred to prepare the radiation curable pressure sensitive adhesive compositions using a dual reactor configuration, with one of the polymers being produced in the first reactor, the other of the polymers being produced in a second reactor, and the tackifier(s) and optional plasticizer(s) being optionally provided, typically at a point after the second reactor, via a side-arm extruder. In this embodiment, radiation curable pressure sensitive compositions can be provided in forms such as pellets, pillows, or any other desired configuration. Examples of such a process which may be adapted in accordance with the teachings of this disclosure to prepare blends of a homogenous linear (higher molecular weight or ultra-low molecular weight) or substantially linear ethylene/α-olefin interpolymer, wax, and optional tackifier, are disclosed in WO 94/00500 and WO 94/01052.

The radiation curable composition of the present invention can be coated from solution or applied molten by any of a variety of coating processes well known in the art including knife coating, roll coating, gravure coating, pattern coating, curtain coating, etc. Useful coating thickness' range from about 12.5 to 500 μm, preferably from about 25 to about 200 μm, and more preferably from 25 to 150 μm.

High viscosity metallocene based composition may be applied molten or cast from a solvent solution and cured with a variety of radiation sources, particularly ultraviolet or electron beam. The low viscosity metallocene based compositions, may be advantageously applied at low application temperature, ranging from room temperature to about 135° C. In this instance, the radiation curable composition preferably has a viscosity less than about 50,000 cPs at 135° C. (275° F.), preferably less than about 30,000 cPs, and more preferably less than about 10,000 cPs.

The preferred adhesive compositions will have a 180° peel of greater than about 1000 g/2.5 cm (2.2 pounds/linear inch), a loop-tack of greater than about 1200 g/2.5 cm$^2$ (2.5 pounds/inch$^2$) and a shear value at room temperature of greater than about 24 hours for a 1 kg load. More preferably, the adhesive compositions exhibit shear values greater than about 24 hours for a 1 kg load at elevated temperatures, 70° C. Most preferably, the peel value is greater than about 2000 g/2.5 linear cm (4.0 pli) and the loop tack in excess of 2000 g/2.5 cm$^2$ (4.5 psi).

A PSA tape can be made from the radiation curable composition of the present invention by coating onto a substrate a composition comprising at least one metallocene polyolefin and exposing the coated substrate to sufficient UV or EB radiation to effectively crosslink the composition to provide a PSA. The tapes may be employed for various application including medical tapes, masking tapes, pressure sensitive labels, laminates of polymeric film and foils, industrial tapes such as automotive tapes as well as highway marking tapes.

Crosslinked compositions derived from the composition of the present invention preferably have a gel content (when corrected for soluble tackifying resins and other additives) in the ranges of from 2 to 95 wt-%, more preferably from 30 to 80 wt-% and most preferably from 50 to 70 wt-%.

A wide range of materials can be used as substrates. Common examples include polyethylene terephthalate, hereinafter PET, various polyolefin and other plastic films such as polycarbonate and polyurethane, woven and non-woven fabrics, metals and metal foils, paper, glass, ceramics, and composite materials comprised of laminates of one more of these materials. The radiation curable composition of the present invention can also be coated onto release liners, such as those described in U.S. Pat. Nos. 4,386,135; 3,957,724 and 2,532,011 and subsequently radiation cured to form adhesive transfer films.

In some applications, primers can be used to improve the adhesion of the composition to some substrates.

For coating applications, the metallocene based composition may be applied to various materials such as films and metals and cured to provide a coating with desired properties such as high cohesive strength, resistance to chemicals such as solvent, oxidative degradation resistance, abrasion resistance, improved moisture and gas barrier properties, as well as combination of such properties.

The invention can be further illustrated by the following non-limiting examples.

EXAMPLES

Generic Description of Tradename Employed in the Examples

| Name | Description | Supplier |
|---|---|---|
| .858 g/cm$^3$ 500 MI | substantially linear ethylene-octene interpolymer | Dow Chemical Co., Freeport, TX |
| .858 g/cm$^3$ 30 MI | substantially linear ethylene-octene interpolymer | Dow Chemical Co., Freeport, TX |
| Eastotac H-100-W | hydrogenated C9 hydrocarbon resin | Eastman Chemicals, Kingsport, TN |
| Kaydol Oil | white mineral oil | Witco, New York, NY |
| 1200 Oil | 1200 viscosity napthenic oil | Various suppliers |
| Irgacure 184 | 1-hydroxycyclohexyl phenyl ketone | Ciba-Geigy, Hawthorne, NY |
| RRM1 | hydroxy terminated aliphatic oligomer reacted 1:1.5 with an isocyanate terminated urethane-acrylate oligomer | H.B. Fuller Co., St. Paul, MN |

Test Methods

Density is measured in accordance with ASTM D-792. The samples are annealed at ambient conditions for 24 hours before the measurement is taken.

Melt index ($I_2$, is measured in accordance with ASTM D-1238, condition 190° C./2.16 kg (formally known as "Condition (E)").

Molecular weight is determined using gel permeation chromatography (GPC) on a Waters 150° C. high temperature chromatographic unit equipped with three mixed porosity columns (Polymer Laboratories 103, 104, 105, and 106), operating at a system temperature of 140° C. The solvent is 1,2,4-trichlorobenzene, from which 0.3 wt-% solutions of the samples are prepared for injection. The flow rate is 1.0 mL/min. and the injection size is 100 microliters.

The molecular weight determination is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Word in Journal of Polymer Science, Polymer Letters, Vol. 6, (621) 1968, incorporated herein by reference) to derive the following equation:

$$M_{polyethylene} = a * (M_{polystyrene})^b.$$

In this equation, a=0.4316 and b=1.0. Weight average molecular weight, $M_w$, is calculated in the usual manner according to the following formula: $M_w = \Sigma w_i * M_i$, where $w_i$ and $M_i$ are the weight fraction and molecular weight, respectively, of the ith fraction eluting from the GPC column.

Melt Viscosity is determined in accordance with the following procedure using a Brookfield Laboratories DVII+ Viscometer in disposable aluminum sample chambers. The spindle used is a SC-27 hot-melt spindle, suitable for measuring viscosities in the range of from about 10 to about 100,000 centipoise. The sample is placed in the chamber, which is in turn inserted into a Brookfield Thermosel and locked into place. The sample chamber has a notch on the bottom that fits the bottom of the Brookfield Thermosel to ensure that the chamber is not allowed to turn when the spindle is inserted and spinning. The sample is heated to the desired temperature, with additional sample being added until the melted sample is about 1 inch (2.5 cm) below the top of the sample chamber. The viscometer apparatus is lowered and the spindle submerged into the sample chamber.

Lowering is continued until brackets on the viscometer align on the Thermosel. The viscometer is turned on, and set to a shear rate which leads to a torque reading in the range of 30% to 60%. The reading is taken after about 30 minutes, or after the value has stabilized.

Peel Testing was done in accordance with PSTC-1, revised August 1985, "Peel Adhesion of Single Coated Pressure-Sensitive Tapes at 180° Angle". The adhesive was coated at a temperature of 350° F. (177° C.) onto 2 mil Mylar™ (polyethylene terephthalate) at the coating thickness depicted in Tables III and IV. The coated Mylar™) was cut into strips 1 inch in width by 6 inches in length (2.5 cm by 15.2 cm). The strips were then adhered to stainless steel plates, recording the average removal force of 4 samples at room temperature (25° C.). The failure mode is also recorded in Tables III and IV.

"C"—Cohesive meaning failure due to separation within the adhesive layer, resulting in a significant amount of adhesive left on the Mylar™ substrate and the stainless steel test panel.

"LT"—Light Transfer meaning a small amount of adhesive transfers to the stainless steel panel, whereas the majority of the adhesive remains on the Mylar™.

"A"—Adhesive meaning the adhesive remains on the Mylar™ substrate.

"Ghosting" meaning the predominantly adhesive transfer with some amount of residue left on the stainless steel panels.

Static Shear was done in accordance with PSTC-7, revised August 1985, "Holding Power of Pressure Sensitive Tapes". The samples were coated as described in the Peel test. The samples were laminated onto a stainless steel test panel with a 4.5 pound (2.0 kg) hand roller and allowed to dwell for 20 minutes prior to testing. A 1.0 kg load was employed, reporting the average of 4 samples and noting the failure mode as described in the Peel test.

Loop Tack was done is accordance with FINAT Test Method No. 9 (FTM 9) The samples were coated as described in the Peel test. The samples were adhered to stainless steel at room temperature, reporting the average of 5 samples and the failure mode as described in the Peel test.

Polymerization of Ultra-Low Molecular Weight Polymers and Waxes

Catalyst Preparation One

Part 1: Preparation of $TiCl_3(DME)1.5$

The apparatus (referred to as R-1) was set-up in the hood and purged with nitrogen; it consisted of a 10 L glass kettle with flush mounted bottom valve, 5-neck head, polytetrafluoroethylene gasket, clamp, and stirrer components (bearing, shaft, and paddle). The necks were equipped as follows: stirrer components were put on the center neck, and the outer necks had a reflux condenser topped with gas inlet/outlet, an inlet for solvent, a thermocouple, and a stopper. Dry, deoxygenated dimethoxyethane (DME) was added to the flask (approx. 5 L). In the drybox, 700 g of $TiCl_3$ was weighed into an equalizing powder addition funnel; the funnel was capped, removed from the drybox, and put on the reaction kettle in place of the stopper. The $TiCl_3$ was added over about 10 minutes with stirring. After the addition was completed, additional DME was used to wash the rest of the $TiCl_3$ into the flask. The addition funnel was replaced with a stopper, and the mixture heated to reflux. The color changed from purple to pale blue. The mixture was heated for about 5 hours, cooled to room temperature, the solid was allowed to settle, and the supernatant was decanted from the solid. The $TiCl_3(DME)_{1.5}$ was left in R-1 as a pale blue solid.

Part 2: Preparation of $[(Me_4C_5)SiMe_2N\text{-}t\text{-}Bu][MgCl]_2$

The apparatus (referred to as R-2) was set-up as described for R-1, except that flask size was 30 L. The head was equipped with seven necks; stirrer in the center neck, and the outer necks containing condenser topped with nitrogen inlet/outlet, vacuum adapter, reagent addition tube, thermocouple, and stoppers. The flask was loaded with 4.5 L of toluene, 1.14 kg of $(Me_4C_5H)SiMe_2NH\text{-}t\text{-}Bu$, and 3.46 kg of 2 M i-PrMgCl in $Et_2O$. The mixture was then heated, and the ether allowed to boil off into a trap cooled to −78° C. After four hours, the temperature of the mixture had reached 75° C. At the end of this time, the heater was turned off and DME was added to the hot, stirring solution, resulting in the formation of a white solid. The solution was allowed to cool to room temperature, the material was allowed to settle, and the supernatant was decanted from the solid. The $[(Me_4C_5)SiMe_2N\text{-}t\text{-}Bu][MgCl]_2$ was left in R-2 as an off-white solid.

Part 3: Preparation of $[(\eta^5\text{-}Me_4C_5)SiMe_2N\text{-}t\text{-}Bu]TiMe_2$ The materials in R-1 and R-2 were slurried in DME (3 L of DME in R-1 and 5 L in R-2). The contents of R-1 were transferred to R-2 using a transfer tube connected to the bottom valve of the 10 L flask and one of the head openings in the 30 L flask. The remaining material in R-1 was washed over using additional DME. The mixture darkened quickly to a deep red/brown color, and the temperature in R-2 rose from 21° C. to 32° C. After 20 minutes, 160 mL of $CH_2Cl_2$ was added through a dropping funnel, resulting in a color change to green/brown. This was followed by the addition of 3.46 kg of 3 M MeMgCl in THF, which caused a temperature increase from 22° C. to 5° C. The mixture was stirred for 30 minutes, then 6 L of solvent was removed under vacuum. Isopar™ E hydrocarbon (6 L) was added to the flask. This vacuum/solvent addition cycle was repeated, with 4 L of solvent removed and 5 L of Isopar™ E hydrocarbon added. In the final vacuum step, an additional 1.2 L of solvent was removed. The material was allowed to settle overnight, then the liquid layer decanted into another 30 L glass kettle (R-3). The solvent in R-3 was removed under vacuum to leave a brown solid, which was re-extracted with Isopar E; this material was transferred into a storage cylinder. Analysis indicated that the solution (17.23 L) was 0.1534 M in titanium; this is equal to 2.644 moles of $[(\eta^5\text{-}Me_4C_5) SiMe_2N\text{-}t\text{-}Bu]TiMe_2$. The remaining solids in R-2 were further extracted with Isopar™ E hydrocarbon, the solution was transferred to R-3, then dried under vacuum and re-extracted with Isopar™ E hydrocarbon. This solution was transferred to storage bottles; analysis indicated a concentration of 0.1403 M titanium and a volume of 4.3 L (0.6032 moles $[(\eta^5\text{-}Me_4C_5)SiMe_2N\text{-}t\text{-}Bu]TiMe_2)$. This gives an overall yield of 3.2469 moles of $[(\eta^5\text{-}Me_4C_5)SiMe2N\text{-}t\text{-}Bu]TiMe_2$, or 1063 g. This is a 72 percent yield overall based on the titanium added as $TiCl_3$.

Catalyst Preparation Two

Part 1: Preparation of $TiCl_3(DME)_{1.5}$

The apparatus (referred to as R-1) was set-up in the hood and purged with nitrogen; it consisted of a 10 L glass kettle with flush mounted bottom valve, 5-neck head, polytetrafluorethylene gasket, clamp, and stirrer components (bearing, shaft, and paddle). The necks were equipped as follows: stirrer components were put on the center neck, and the outer necks had a reflux condenser topped with gas inlet/outlet, an inlet for solvent, a thermocouple, and a stopper. Dry, deoxygenated dimethoxyethane (DME) was added to the flask (approx. 5.2 L). In the drybox, 300 g of TiCl$_3$ was weighed into an equalizing powder addition funnel; the funnel was capped, removed from the drybox, and put on the reaction kettle in place of the stopper. The TiCl$_3$ was added over about 10 minutes with stirring. After the addition was completed, additional DME was used to wash the rest of the TiCl$_3$ into the flask. This process was then repeated with 325 g of additional TiCl$_3$, giving a total of 625 g. The addition funnel was replaced with a stopper, and the mixture heated to reflux. The color changed from purple to pale blue. The mixture was heated for about 5 hours, cooled to room temperature, the solid was allowed to settle, and the supernatant was decanted from the solid. The TiCl$_3$(DME)$_{1.5}$ was left in R-1 as a pale blue solid.

Part 2: Preparation of [(Me$_4$C$_5$)SiMe$_2$N-t-Bu][MgCl]$_2$

The apparatus (referred to as R-2) was set-up as described for R-1, except that flask size was 30 L. The head was equipped with seven necks; stirrer in the center neck, and the outer necks containing condenser topped with nitrogen inlet/outlet, vacuum adapter, reagent addition tube, thermocouple, and stoppers. The flask was loaded with 7 L of toluene, 3.09 kg of 2.17 M i-PrMgCl in Et$_2$O, 250 mL of THF, and 1.03 kg of (Me$_4$C$_5$H)SiMe$_2$NH-t-Bu. The mixture was then heated, and the ether allowed to boil off into a trap cooled to −78° C. After three hours, the temperature of the mixture had reached 80° C., at which time a white precipitate formed. The temperature was then increased to 90° C. over 30 minutes and held at this temperature for 2 hours. At the end of this time, the heater was turned off, and 2 L of DME was added to the hot, stirring solution, resulting in the formation of additional precipitate. The solution was allowed to cool to room temperature, the material was allowed to settle, and the supernatant was decanted from the solid. An additional wash was done by adding toluene, stirring for several minutes, allowing the solids to settle, and decanting the toluene solution. The [(Me$_4$C$_5$)SiMe$_2$N-t-Bu][MgCl]$_2$ was left in R-2 as an off-white solid.

Part 3: Preparation of [(η5-Me$_4$C$_5$)SiMe$_2$N-t-Bu]Ti(η$^4$-1,3-pentadiene)

The materials in R-1 and R-2 were slurried in DME (the total volumes of the mixtures were approximately 5 L in R-1 and 12 L in R-2). The contents of R-1 were transferred to R-2 using a transfer tube connected to the bottom valve of the 10 L flask and one of the head openings in the 30 L flask. The remaining material in R-1 was washed over using additional DME. The mixture darkened quickly to a deep red/brown color. After 15 minutes, 1050 mL of 1,3-pentadiene and 2.60 kg of 2.03 M n-BuMgCl in THF were added simultaneously. The maximum temperature reached in the flask during this addition was 53° C. The mixture was stirred for 2 hours, then approximately 11 L of solvent was removed under vacuum. Hexane was then added to the flask to a total volume of 22 L. The material was allowed to settle, and the liquid layer (12 L) was decanted into another 30 L glass kettle (R-3). An additional 15 liters of product solution was collected by adding hexane to R-2, stirring for 50 minutes, again allowing to settle, and decanting. This material was combined with the first extract in R-3. The solvent in R-3 was removed under vacuum to leave a red/black solid, which was then extracted with toluene. This material was transferred into a storage cylinder. Analysis indicated that the solution (11.75 L) was 0.255 M in titanium; this is equal to 3.0 moles of [(η$^5$-Me$_4$C$_5$)SiMe$_2$N-t-Bu]Ti(η$^4$-1,3-pentadiene) or 1095 g. This is a 74 percent yield based on the titanium added as TiCl$_3$.

Polymers A–D and Waxes 1–3 were produced in a solution polymerization process using a continuously stirred reactor. Polymers A, B, and C, and Wax 1 were each stabilized with 1250 ppm calcium stearate, 500 ppm Irganox™ 1076 hindered polyphenol stabilizer (available from Ciba-Geigy Corporation), and 800 ppm PEPQ (tetrakis(2,4-di-t-butylphenyl)-4,4'-biphenylene diphosphonite) (available from Clariant Corporation). Polymer D and Waxes 2 and 3 were each stabilized with 500 ppm Irganox™ 1076 hindered polyphenol stabilizer, 800 ppm PEPQ, and 100 ppm water (as a catalyst kill agent).

The ethylene and the hydrogen were combined into one stream before being introduced into the diluent mixture, a mixture of C$_8$–C$_{10}$ saturated hydrocarbons, for example, ISOPAR-E hydrocarbon mixture (available from Exxon Chemical Company) and the comonomer. For polymers A, B, C, and D and for Waxes 1 and 2 the comonomer was 1-octene; Wax 3 had no comonomer. The reactor feed mixture was continuously injected into the reactor.

The metal complex and cocatalysts were combined into a single stream and were also continuously injected into the reactor. For Polymers A, B, and C and Wax 1, the catalyst was as prepared in Catalyst Preparation One set forth above. For Polymer D and Waxes 2 and 3, the catalyst was as prepared in Catalyst Preparation Two set forth above. For each Polymer and Wax, the co-catalyst was tris (pentafluorophenyl)borane, available as a 3 wt-% solution in Isopar™-E mixed hydrocarbon, from Boulder Scientific. Aluminum was provided in the form of a solution of modified methylalumoxane (MMAO Type 3A) in heptane, which is available at a 2 wt-% aluminum concentration from Akzo Nobel Chemical Inc.

Sufficient residence time was allowed for the metal complex and cocatalyst to react prior to introduction into the polymerization reactor. In each polymerization reaction, the reactor pressure was held constant at about 475 psig (3.3 MPa). Ethylene content of the reactor, in each polymerization, after reaching steady state, was maintained at the conditions specified in Table I.

After polymerization, the reactor exit stream was introduced into a separator where the molten polymer is separated from the unreacted comonomer(s), unreacted ethylene, unreacted hydrogen, and diluent mixture stream. The molten polymer was subsequently strand chopped or pelletized, and, after being cooled in a water bath or pelletizer, the solid pellets were collected. Table I describes the polymerization conditions and the resultant polymer properties.

Polymers E and F and Wax 4 were produced in a solution polymerization process using a well-mixed recirculating loop reactor. Each polymer was stabilized with 2000 ppm Irganox™ 1076 hindered polyphenol stabilizer (available from Ciba-Geigy Corporation) and 35 ppm deionized water (as a catalyst kill agent).

The ethylene and the hydrogen (as well as any ethylene and hydrogen which were recycled from the separator, were combined into one stream before being introduced into the diluent mixture, a mixture of C$_{8-C10}$ saturated hydrocarbons, for example, Isopar™-E hydrocarbon (available from Exxon Chemical Company) and the comonomer 1-octene.

The metal complex and cocatalysts were combined into a single stream and were also continuously injected into the reactor. The catalyst was as prepared in Catalyst Description Two set forth above; the primary cocatalyst was tri(pentafluorophenyl)borane, available from Boulder Scientific as a 3 wt percent solution in ISOPAR-E mixed hydrocarbon; and the secondary cocatalyst was modified methylalumoxane (MMAO Type 3A), available from Akzo Nobel Chemical Inc. as a solution in heptane having 2 wt percent aluminum.

Sufficient residence time was allowed for the metal complex and cocatalyst to react prior to introduction into the polymerization reactor. The reactor pressure was held constant at about 475 psig (3.3 MPa).

After polymerization, the reactor exit stream was introduced into a separator where the molten polymer was separated from the unreacted comonomer(s), unreacted ethylene, unreacted hydrogen, and diluent mixture stream, which was in turn recycled for combination with fresh comonomer, ethylene, hydrogen, and diluent, for introduction into the reactor. The molten polymer was subsequently strand chopped or pelletized, and, after being cooled in a water bath or pelletizer, the solid pellets were collected. Table II describes the polymerization conditions and the resultant polymer properties.

TABLE I

| | Polymer A | Polymer B | Polymer C | Polymer D | Wax 1 | Wax 2 | Wax 3 |
|---|---|---|---|---|---|---|---|
| Ethylene feed (lb/hr (kg/hr)) | 2.0 (0.9) | 2.0 (0.9) | 2.0 (0.9) | 3.0 (1.4) | 3.0 (1.4) | 3.0 (1.4) | 3.0 (1.4) |
| Comonomer:olefin ratio (mole percent) | 12.40 | 8.50 | 12.50 | 9.10 | 0.40 | 1.24 | 0.00 |
| Hydrogen:ethylene ratio (mole percent) | 0.26 | 0.66 | 1.26 | 0.54 | 1.60 | 2.14 | 2.14 |
| Diluent:ethylene ratio (weight basis) | 10.60 | 9.30 | 11.10 | 9.99 | 5.90 | 7.69 | 7.70 |
| Catalyst metal concentration (ppm) | 4 | 2 | 4 | 3 | 5 | 32 | 32 |
| Catalyst flow rate (lb/hr (kg/hr)) | 0.272 (0.123) | 0.386 (0.175) | 0.428 (0.194) | 0.450 (0.205) | 0.626 (0.285) | 0.304 (0.138) | 0.294 (0.134) |
| Co-catalyst concentration (ppm) | 88 | 44 | 88 | 88 | 353 | 1430 | 1430 |
| Co-catalyst flow rate (lb/hr (kg/hr)) | 0.396 (0.180) | 0.561 (0.254) | 0.624 (0.283) | 0.490 (0.223) | 0.284 (0.129) | 0.219 (0.100) | 0.211 (0.096) |
| Aluminum concentration (ppm) | 10 | 5 | 10 | 9.8 | 20 | 120.0 | 120.0 |
| Aluminum flow rate (lb/hr) | 0.375 (0.170) | 0.528 (0.240) | 0.590 (0.268) | 0.468 (0.213) | 0.534 (0.243) | 0.323 (0.147) | 0.311 (0.141) |
| Reactor temperature (° C.) | 110 | 110 | 110 | 110 | 140 | 110 | 110 |
| Ethylene concentration in reactor exit stream (wt-%) | 1.80 | 2.99 | 1.65 | 1.71 | 4.41 | 1.80 | 1.69 |
| Polymer density (g/cm$^3$) | 0.875 | 0.897 | 0.870 | 0.883 | 0.968 | 0.948 | 0.960 |
| Polymer melt viscosity at 177° C. (350° F.) (cPs) | 39,000* | 5200 | 355 | 5000 | 395 | 350 | 512 |
| Polymer melt index ($I_2$ at 190° C.) | 246 | 1500* | 16,000* | 1500* | 15,000* | 16,000* | 12,000* |
| Polymer Mw | 30,100 | 15,600 | 7,900 | 16,200 | 7,300 | 6,900 | 7,400 |
| Polymer Mn | 17,100 | 8,700 | 4,300 | 8,200 | 3,700 | 3,200 | 3,200 |
| Polymer Mw/Mn | 1.76 | 1.79 | 1.84 | 1.98 | 1.97 | 2.16 | 2.31 |
| Peak crystallization temperature by DSC (° C.) | 55.73 | 59.05 | 78.57 | 69.27 | 114.76 | 109.88 | 116.39 |
| Peak melting temperature by DSC (° C.) | 68 | 67 | 91.04 | 81.97 | 127.6 | 120.5 | 131.11 |
| Total percent crystallinity by DSC | 18.94 | 19.55 | 36.3 | 28.18 | 79.62 | 72.81 | 72.84 |

*Calculated on the basis of melt viscosity correlations in accordance with the formula:
$I_2 = 3.6126(10^{\log(\eta)-6.6928)/-1.1363}) - 9.3185$, where $\eta$ = melt viscosity at 177° C. (350° F.)

TABLE II

| | Polymer E | Polymer F | Wax 4 |
|---|---|---|---|
| Ethylene fresh feed rate (lbs/hr (kg/hr)) | 140 (63.5) | 140 (63.5) | 140 (63.5) |
| Total ethylene feed rate (lbs/hr (kg/hr)) | 146.2 (66.32) | 146.17 | 146.5 (66.45) |
| Fresh octene feed rate (lbs/hr (kg/hr)) | 45.4 (20.6) | 49.5 (22.4) | 12.67 (5.75) |
| Total octene feed rate (lbs/hr (kg/hr)) | Not determined | 112 (50.8) | 32.9 (14.9) |
| Total octene concentration (wt-%) | Not determined | 11.4 | 3.36 |
| Fresh hydrogen feed rate (standard cm$^3$/min.) | 4025 | 5350 | 16100 |
| Solvent and octene feed rate (lbs/hr (kg/hr)) | 840 (381) | 839.4 (381) | 840 (381) |
| Ethylene conversion rate (wt-%) | 90.7 | 90.3 | 88.26 |
| Reactor temperature (° C.) | 109.86 | 119.8 | 134.3 |
| Feed temperature (° C.) | 15 | 15 | 15.3 |
| Catalyst concentration (ppm) | 70 | 70 | 70 |
| Catalyst flow rate (lbs/hr (kg/hr)) | 0.725 (0.329) | 1.265 | 4.6 (2.1) |
| Primary cocatalyst concentration (ppm) | 1200 | 2031 | 1998 |
| Primary cocatalyst flow rate (lbs/hr (kg/hr)) | 2.96 (1.34) | 1.635 | 5.86 (2.66) |
| Titanium:boron molar ratio | 2.96 | 3.48 | 2.897 |
| Secondary cocatalyst concentration (ppm) | 198 | 198 | 198 |
| Secondary cocatalyst flow rate (lbs/hr (kg/hr)) | 0.718 (0.326) | 1.258 (0.571) | 3.7 (1.7) |
| Titanium:aluminum molar ratio | 5 | 4.986 | 4.037 |
| Product density (g/cm$^3$) | 0.8926 | 0.8925 | 0.9369 |
| Product melt viscosity at 177° C. (350° F.) | 12,500 | 4,000 | 400 |
| Polymer melt index ($I_2$ at 190° C.)* | 686* | 1,900* | 14,000* |
| Polymer $M_n$ | 12,300* | 8,900* | 4,700* |

*Calculated on the basis of melt viscosity correlations in accordance with the formulas:
$I_2 = 3.6126(10^{\log(\eta)-6.6928)/-1.1363}) - 9.3185$, $M_n = 10^{[(\log\eta+10.46)/3.56]}$
where $\eta$ = melt viscosity at 177° C. (350° F.).

TABLE III

| Ingredient | Ex. 1 | Ex. 2 | Ex. 3 | Ex. 4 | Ex. 5 |
|---|---|---|---|---|---|
| .858 g/cm³, 500 MI | 100 | 90 | 35 | | |
| .858 g/cm³, 30 MI | | | | 35 | 36 |
| Eastotac H-100-W | | 10 | 40 | 40 | 41 |
| Kaydol Oil | | | 25 | 25 | 23 |
| Viscosity @ 350° F. | | | | 9720 | 11,160 |
| Coating Thickness | 3 mils | 4 mils | 5 mils | 1 mil | 1 mil |
| 180° Peel (g/inch) | | | | | |
| Initial (uncured) | 35 | 210 | 796 | 753 | 968 |
| Initial Failure Mode | C | LT | C | C | C |
| 2 Mrad Dosage | 55 | 181 | 804 | 806 | 911 |
| 2 Mrad Failure Mode | C | LT | C | C | C |
| 4 Mrad Dosage | 62 | 190 | 891 | | |
| 4 Mrad Failure Mode | C | LT | C | | |
| 6 Mrad Dosage | 19 | 127 | 756 | | |
| 6 Mrad Failure Mode | C | C | C | | |
| 8 Mrad Dosage | 59 | 182 | 595 | | |
| 8 Mrad Failure Mode | LT | C | C | | |
| Static Shear (min.) | | | | | |
| Initial (uncured) | 1037 | 2306 | 151 | 272 | 591 |
| Initial Failure Mode | C | LT | C | LT | LT |
| 2 Mrad Dosage | 1779 | 3440 | 321 | 329 | 680 |
| 2 Mrad Failure Mode | LT | LT/A | LT/A | LT/A | LT |
| 4 Mrad Dosage | 1885 | 2957 | 609 | 222 | 307 |
| 4 Mrad Failure Mode | LT | | LT/A | LT | LT/A |
| 6 Mrad Dosage | 452 | | 221 | 138 | |
| 6 Mrad Failure Mode | LT | | LT/A | LT | |
| 8 Mrad Dosage | 318 | | 99 | | |
| 8 Mrad Failure Mode | LT | | C | | |

Examples 1–5 are directed to EB cured compositions comprising metallocene polyolefins. Example 1–3 are graphically illustrated in Figures A–C. The 180° Peel is representative of the surface tackiness, adhesive strength, and viscoelastic characteristics, whereas the Static Shear is representative of the cohesive strength. Example 1 depicts an increase in Static Shear from about 1000 min to about 1800 min with an EB dosage ranging from about 2 to 4 Mrads. This composition has utility for low peel, high shear adhesive application. Further, it is surmised that the surface tackiness can be eliminated by the addition of detackifying ingredients such as waxes without hindering the increase in static shear. In this instance the composition is surmised to be amenable to coating applications.

Example 2 of Figure B depicts a similar increase in static shear with essentially no decrease in 180° Peel strength. Accordingly, this composition is also expected to have utility for low peel, high cohesive strength adhesive applications. As in the case of Example 1, for coating applications, the surface tackiness may be eliminated with additional ingredients.

Example 3 of Figure C demonstrates an increase in shear in excess of about 5 times that of the uncured sample. Concurrently, about a 15% increase in peel is also exhibited. Hence, an EB dosage of 4 Mrad maximizes both the peel and shear concurrently.

TABLE IV

| | Ex.6 | Ex.7 |
|---|---|---|
| Ingredient | | |
| .858 g/cm³, 500 MI | 100 | 80 |
| Irgacure 184 | 1 | 0.4 |
| RRM 1 | | 17.4 |
| Coating Thickness | | 4 mils |
| 180° Peel (g/inch) | | |
| Initial (uncured) | 27 | 47.2 |
| Failure Mode | A | A |
| 1 pass | 139 | 80.2 |
| Failure Mode | A | A |
| Static Shear (min.) | | |
| Initial (uncured) | 1302 | 310 |
| Failure Mode | Ghosting | C |
| 1 pass | 1896 | 1245 |
| Failure Mode | Ghosting | C |
| Loop Tack (lbs.) | | |
| Initial (uncured) | 1.9 | 2.7 |
| Failure Mode | C | C |
| 1 pass | 2.1 | 1.9 |
| Failure Mode | C | C |

| | UV A | UV B | UV C | UV V |
|---|---|---|---|---|
| mJ/cm2 | 609 | 487 | 60 | 375 |
| mW/cm2 | 1598 | 1537 | 155 | 1186 |

*Power-Puck ™ for each UV pass

Examples 6–7 are directed toward UV curable compositions comprising metallocene polyolefins. Example 6 employs one part photoinitiator in combination with the metallocene polyolefin. A substantial increase in 180° Peel and Static Shear is obtained with a single pass of UV radiation* while maintaining Loop Tack. Example 7 employs about 20 parts of a second radiation responsive material formed by reacting 1 equivalence of Kraton L-1203, a liquid ethylene-butylene hydroxyl terminated copolymer available from Shell Chemical Co., with 1.5 equivalents of an isocyanate terminated urethane acrylated oligomer to functionalize the hydroxyl group of the Kraton oligomer. After a single pass of UV radiation, this sample exhibits approximately a two-fold increase in 180° Peel concurrently with a four-fold increase in Static Shear and a decrease in Loop Tack. The performance of both Examples 6 and 7 can be expected to be further optimized by judicious compounding by one skilled in the art.

Table V represents radiation curable laminating composition comprising metallocene polyolefins.

TABLE V

| | Example 8 | Example 9 |
|---|---|---|
| Dow 0.87 g/cc/5000 cps | 100 | 70 |
| Escorez 5615 | — | 30 |
| Epolene C-10 (0.906 g/cc) | — | — |
| G @ 20 C | 4.25 E7 | 2.0 E7 |
| Radiation Dose | | |
| None | 0.08 lb/in | 0.35 |
| 1 Mrad | 0.17 lb/in | 0.34 |
| 3 Mrad | 0.15 lb/in | 0.44 |
| 5 Mrad | 0.16 lb/in | 0.40 |

0.1–0.2 mil adhesive was applied to 2 mil PET and then heated sealed to second film of 2.0 mil PET at 350° F. (177° C.). These film laminates were then irradiated with Electron Beam radiation using 175 kilo Volts at 1,3,5 Mrads and tested for 180 peel strength at 12 inches/minute.

The adhesion of metallocene catalyzed polyolefins of 0.87 density is attributable to the low modulus or stiffness due to low inherent crystallinity. Irradiation with EB enhances this adhesion as exhibited by examples 8 and 9. The lowest modulus sample (Ex. 9) demonstrates the best performance. Ideally, peel values of greater than 1 lb/inch and preferably great enough to result in film tear are desired for film laminating. Adhesion is expected to be enhanced to this level by the addition of some unsaturated materials such as liquid polyisoprene. An example of this type of material is Isolene 400 from Elementis. Additionally, use of hydrogenated rosin such as Foral NC or Foral AX from Hercules is expected to result in dramatic improvements in specific adhesion.

What is claimed is:

1. A composition radiation-curable to an adhesive comprising from about 15 wt-% to 100 wt-% of at least one homogeneous linear or substantially linear metallocene interpolymer of ethylene and at least one methylidyne group containing alpha-olefin, said interpolymer having a density ranging from about 0.850 g/cm$^3$ to about 0.890 g/cm$^3$.

2. A composition radiation-curable to a self-supporting film comprising from about 15 wt-% to 100 wt-% of at least one homogeneous linear or substantially linear metallocene interpolymer of ethylene and at least one methylidyne group containing alpha-olefin, said interpolymer having a density ranging from about 0.850 g/cm$^3$ to about 0.890 g/cm$^3$.

3. The composition of claim 2 further comprising at least one wax.

4. The composition of claim 2 wherein the interpolymer has ranges from having a melt index of greater than about 10 g/10 min.

5. A composition radiation-curable to a coating comprising from about 15 wt-% to 100 wt-% of at least one homogeneous linear or substantially linear metallocene interpolymer of ethylene and at least one methylidyne group containing alpha-olefin, said interpolymer having a density ranging from about 0.850 g/cm$^3$ to about 0.890 g/cm$^3$.

6. The composition of claim 5 wherein the interpolymer has a melt index of greater than about 10 g/10 min.

7. The composition of claim 1 further comprising up to 70 wt-% of a tackifying resin.

8. The composition of claim 1 further comprising up to 40 wt-% of a plasticizer.

9. The composition of claim 1 further comprising a second radiation responsive component selected from the group consisting of polyisoprenes, hydroxy-terminated ethylene-butylene copolymer, (meth)acrylated polyolefins, (meth)acrylated polyesters, (meth)acrylic monomers, (meth) acrylated block oligomers, hydroxy-functional ethylene-butylene oligomers, (meth)acrylated urethanes (meth) acrylated polyamides, and mixtures thereof.

10. The composition of claim 1 further comprising at least one photoinitiator.

11. The composition of claim 1 further comprising at least one photoinduced coupling agent.

12. The composition of claim 1 wherein said composition is radiation curable to a pressure sensitive adhesive.

13. The composition of claim 1 wherein the metallocene polyolefin comprises a metallocene polyolefin backbone and at least one grafted portion attached to the backbone selected from the group consisting of high density polyethylene, wax, and mixtures thereof.

14. The composition of claim 1 wherein the comonomer of the metallocene polyolefin is selected from the group consisting of 3-methylpentene, 4-methyl heptene, 4,5 dimethyl 1-hexene, and mixtures thereof.

15. An article comprising a substrate coated with adhesive composition of claim 1.

16. The composition of claim 1 wherein the interpolymer has a melt index of greater than about 10 g/10 min.

17. A radiation-curable composition comprising from about 15 wt-% to 100 wt-% of at least one homogeneous linear or substantially linear metallocene interpolymer of ethylene and at least one methylidyne group containing alpha-olefin, said interpolymer having a density ranging from about 0.850 g/cm$^3$ to about 0.890 g/cm$^3$.

18. The composition of claim 7 wherein the interpolymer has a melt index of greater than about 10 g/10 min.

19. A method of curing radiation-curable composition on a substrate comprising the steps of:

a) providing a composition comprising at least one homogeneous linear or substantially linear metallocene interpolymer of ethylene and at least one methylidyne group containing alpha-olefin, said interpolymer having a density ranging from about 0.850 g/cm$^3$ to about 0.890 g/cm$^3$;

b) coating said composition onto a substrate; and c) exposing said composition to an effective amount of radiation for curing.

20. The method of claim 19 wherein said composition is radiation curable to a pressure sensitive adhesive.

21. The method of claim 19 wherein said composition is radiation curable to a coating.

22. The method of claim 19 wherein the interpolymer has a melt index of greater than about 10 g/10 min.

23. A composition radiation curable to a gel comprising:

a) from about 15 wt-% to 90 wt-% of at least one metallocene polyolefin having a mean comonomer content ranging from about 10 to about 20 mole percent;

b) from about 10 wt-% to about 70 wt-% of an oil; and c) from 0 to about 30 wt-% of a tackifying resin.

24. A composition radiation-curable to an adhesive comprising from about 15 wt-% to about 100 wt-% of at least one homogeneous linear or substantially linear ethylene/alpha-olefin metallocene interpolymer having a density ranging from about 0.850 g/cm$^3$ to about 0.890 g/cm$^3$ and an effective amount of reactive hydrogen atoms on tertiary carbon atoms.

25. A composition radiation-curable to a self-supporting film comprising from about 15 wt-% to about 100 wt-% of at least one homogeneous linear or substantially linear ethylene/alpha-olefin metallocene interpolymer having a density ranging from about 0.850 g/cm$^3$ to about 0.890 g/cm$^3$ and an effective amount of reactive hydrogen atoms on tertiary carbon atoms.

26. A composition radiation-curable to a coating comprising from about 15 wt-% to about 100 wt-% of at least one homogeneous linear or substantially linear ethylene/alpha-olefin metallocene interpolymer having a density ranging from about 0.850 g/cm$^3$ to about 0.890 g/cm$^3$ and an effective amount of reactive hydrogen atoms on tertiary carbon atoms.

* * * * *

UNITED STATES PATENT AND TRADEMARK OFFICE
CERTIFICATE OF CORRECTION

PATENT NO.    : 6,339,112 B1
DATED         : January 15, 2002
INVENTOR(S)   : Thomas F. Kauffman, John P. Baetzold and Margarita Acevedo It is certified that error appears in the above-identified patent and that said Letters Patent is hereby corrected as shown below:

Column 5,
Line 29, "preeferably" should be -- preferably --

Column 13,
Line 62, "Generie Description of Tradename" should be -- Generic Description of Tradename --

Column 14,
Line 4, "Generie Description of Tradename" should be -- Generic Description of Tradename --

Column 18,
Line 62, "a mixture of $C_8$-c10 saturated" should be -- a mixture of $C_8$-$C_{10}$ saturated --

Column 24,
Line 9, "The composition of claim 7 wherein" should be -- The composition of claim 17 wherein --

Signed and Sealed this

Eleventh Day of March, 2003

JAMES E. ROGAN
*Director of the United States Patent and Trademark Office*